(12) United States Patent
Siess et al.

(10) Patent No.: US 11,724,092 B2
(45) Date of Patent: *Aug. 15, 2023

(54) BLOOD PUMP

(71) Applicant: Abiomed Europe Gmbh, Aachen (DE)

(72) Inventors: Thorsten Siess, Aachen (DE); Walid Aboulhosn, Aachen (DE)

(73) Assignee: ABIOMED EUROPE GMBH, Aachen (DE)

(*) Notice: Subject to any disclaimer, the term of this patent is extended or adjusted under 35 U.S.C. 154(b) by 201 days.

This patent is subject to a terminal disclaimer.

(21) Appl. No.: 17/016,902

(22) Filed: Sep. 10, 2020

(65) Prior Publication Data

US 2020/0405933 A1 Dec. 31, 2020

Related U.S. Application Data

(63) Continuation of application No. 15/739,317, filed as application No. PCT/EP2016/064562 on Jun. 23, 2016, now Pat. No. 10,799,626.

(30) Foreign Application Priority Data

Jun. 23, 2015 (EP) ..................................... 15173290

(51) Int. Cl.
*A61M 60/833* (2021.01)
*A61M 60/135* (2021.01)
(Continued)

(52) U.S. Cl.
CPC ........ *A61M 60/135* (2021.01); *A61M 60/157* (2021.01); *A61M 60/221* (2021.01);
(Continued)

(58) Field of Classification Search
CPC .............. A61M 60/135; A61M 60/157; A61M 60/221; A61M 60/232; A61M 60/237;
(Continued)

(56) References Cited

U.S. PATENT DOCUMENTS 5,092,844 A * 3/1992 Schwartz ............ A61M 1/1005
600/16
5,163,910 A 11/1992 Schwartz et al.
(Continued)

FOREIGN PATENT DOCUMENTS

CA 2292432 A1 12/1998
CN 1268894 A 10/2000
(Continued)

OTHER PUBLICATIONS

Office Action issued in corresponding Japanese Patent Application No. 2021-015628 dated Jan. 18, 2022, 6 pp.
(Continued)

*Primary Examiner* — Eugene T Wu
(74) *Attorney, Agent, or Firm* — Botos Churchill IP Law LLP

(57) ABSTRACT

A blood pump comprises a pump casing having a blood flow inlet and a blood flow outlet, and an impeller arranged in said pump casing so as to be rotatable about an axis of rotation. The impeller has blades sized and shaped for conveying blood from the blood flow inlet to the blood flow outlet. The blood pump also has an outflow cannula having an upstream end portion, a downstream end portion and an intermediate portion extending between the upstream end portion and the downstream end portion. The upstream end portion of the outflow cannula is connected to the pump casing such that blood is conveyed from the blood flow outlet of the pump casing into and through the intermediate portion of the outflow cannula towards the downstream end portion of the outflow cannula, wherein the downstream end portion has a blood flow outlet through which blood can exit the outflow cannula. At least a portion of the intermediate portion of the outflow cannula has an outer diameter that is larger than an outer diameter of the pump casing.

23 Claims, 11 Drawing Sheets

(51) Int. Cl.
*A61M 60/232* (2021.01)
*A61M 60/221* (2021.01)
*A61M 60/237* (2021.01)
*A61M 60/411* (2021.01)
*A61M 60/157* (2021.01)
*A61M 60/148* (2021.01)
*A61M 60/414* (2021.01)
*A61M 60/13* (2021.01)
*A61M 60/33* (2021.01)

(52) U.S. Cl.
CPC ........ *A61M 60/232* (2021.01); *A61M 60/237* (2021.01); *A61M 60/411* (2021.01); *A61M 60/833* (2021.01); *A61M 60/13* (2021.01); *A61M 60/148* (2021.01); *A61M 60/33* (2021.01); *A61M 60/414* (2021.01)

(58) Field of Classification Search
CPC .. A61M 60/411; A61M 60/833; A61M 60/13; A61M 60/148; A61M 60/33; A61M 60/414
See application file for complete search history.

(56) References Cited

U.S. PATENT DOCUMENTS

| | | | |
|---|---|---|---|
| 5,911,685 A * | 6/1999 | Siess | F04D 29/0467 |
| | | | 600/16 |
| 5,964,694 A | 10/1999 | Siess et al. | |
| 5,967,744 A | 10/1999 | Danner | |
| 6,210,318 B1 | 4/2001 | Lederman | |
| 6,390,969 B1 | 5/2002 | Bolling et al. | |
| 6,533,716 B1 | 3/2003 | Schmitz-Rode et al. | |
| 6,544,216 B1 | 4/2003 | Sammler et al. | |
| 7,011,620 B1 | 3/2006 | Siess | |
| 8,814,933 B2 | 8/2014 | Siess | |
| 10,799,626 B2 | 10/2020 | Siess et al. | |
| 2003/0009145 A1 * | 1/2003 | Struijker-Boudier | |
| | | | A61K 9/0019 |
| | | | 604/500 |
| 2003/0135086 A1 | 7/2003 | Khaw et al. | |
| 2004/0044266 A1 | 3/2004 | Siess et al. | |
| 2006/0183963 A1 | 8/2006 | Weizman et al. | |
| 2009/0093796 A1 * | 4/2009 | Pfeffer | A61M 1/12 |
| | | | 604/530 |
| 2010/0056849 A1 | 3/2010 | Mohl | |
| 2012/0041255 A1 | 2/2012 | Delgado | |
| 2013/0303831 A1 | 11/2013 | Evans | |
| 2014/0012065 A1 * | 1/2014 | Fitzgerald | A61M 1/1008 |
| | | | 600/16 |
| 2015/0051435 A1 | 2/2015 | Siess et al. | |
| 2016/0022890 A1 * | 1/2016 | Schwammenthal | A61F 2/07 |
| | | | 600/17 |

FOREIGN PATENT DOCUMENTS

| | | |
|---|---|---|
| DE | 19613565 C1 | 7/1997 |
| DE | 102004054714 A1 | 5/2006 |
| JP | 2018525064 A | 9/2018 |
| JP | 6833734 B2 | 2/2021 |
| WO | 2014141284 A2 | 9/2014 |
| WO | 2014164292 A1 | 10/2014 |

OTHER PUBLICATIONS

ISR (PCT/EP2016/064562) dated Aug. 9, 2016 (5 pages).
Office Action for corresponding JP Application No. 2021-015628 dated Jun. 29, 2022, (15 pages).
Office Action from corresponding Japanese Patent Application No. 2021-015628 dated Feb. 7, 2023 (5 pages).
Office Action for CN Application No. 202010313535.X, dated Aug. 1, 2022 (24 pages).
Office Action issued in corresponding Chinese Patent Application No. 202010313535.X dated May 11, 2023 (12 pp.).

* cited by examiner

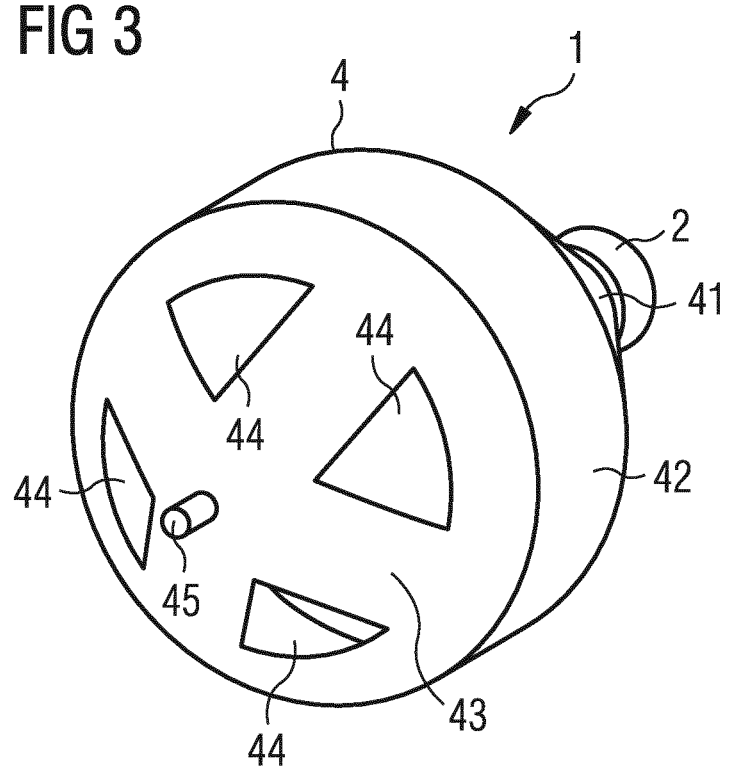

BLOOD PUMP

CROSS-REFERENCE TO RELATED APPLICATIONS

The present application is a continuation of U.S. patent application Ser. No. 15/739,317, filed Dec. 22, 2017, now U.S. Pat. No. 10,799,626, which is a national phase entry under 35 U.S.C. § 371 of International Application No. PCT/EP2016/064562, filed Jun. 23, 2016, published in English, which claims priority from European Patent Application No. 15173290.6, filed Jun. 23, 2015, all of which are incorporated herein by reference in their entirety.

BACKGROUND

This invention relates to a blood pump and method to support a blood flow in a patient's blood vessel, for instance in a renal vein or coronary artery.

Blood pumps of different types are known, such as axial blood pumps, centrifugal blood pumps or mixed-type blood pumps, where the blood flow is caused by both axial and radial forces. Blood pumps may be inserted into a patient's vessel such as the aorta by means of a catheter, or may be placed in the thoracic cavity. Blood pumps are also known for renal use, where the blood pump is placed in a patient's renal vein to support blood flow from the patient's kidney towards the inferior vena cava to prevent renal failure. A blood pump typically comprises a pump casing having a blood flow inlet and a blood flow outlet connected by a passage. In order to cause a blood flow along the passage from the blood flow inlet to the blood flow outlet an impeller is rotatably supported within the pump casing, with the impeller being provided with blades for conveying blood.

It is desirable to avoid a backflow of the blood in a direction opposite the conveying direction of the blood pump. Therefore, means for occluding the vessel in the region of the blood pump, such as balloons that contact the inner wall of the vessel to occlude it or other means that act like a check valve, are known e.g. from DE 196 13 565 C1 or U.S. Pat. No. 5,163,910. It is also known to provide an expandable pump casing that is sized and shaped to contact the inner wall of the vessel, as disclosed in WO 2014/141284 A2.

Another pumping device is disclosed in U.S. Pat. No. 5,163,910, which includes a combination of a pump and an occlusive balloon that are used in conjunction to occlude a vessel by inflating the circumferential balloon while activating the pump to pump blood through the central lumen. However, although such a device can occlude a vessel and forcibly deliver blood through the central lumen, the size of the central catheter is very small relative to the occluded vessel and a limited flow could be delivered by the pump without causing significant blood damage or risk the formation of blood clots due to severe blood damage. The central lumen size is limited due to the fact that the circumferential balloon occupies a significant portion of the overall device diameter. Therefore, little space is left for the central lumen. This becomes more and more apparent as the target vessel becomes small.

Moreover, blood pumps are known from DE 10 2004 054 714 A1 and U.S. Pat. No. 6,533,716 B1 that have an outflow cannula connected to the pump casing, whereby the blood is pumped into and through the outflow cannula from an upstream end portion to a downstream end portion where the blood exits the outflow cannula through a blood flow outlet. The outflow cannula may have an intermediate portion extending between the upstream and downstream end portions. A blood pump's outflow cannula may for instance be placed through the aortic valve while the pump casing is placed inside the left ventricle. If parts of the blood pump contact the inner wall of a patient's vessel, care has to be taken not to harm the vessel.

Other devices for treating blood vessels of a patient are known, in particular devices for dilating a vessel suffering from a stenosis or drug eluting devices, i.e. devices that are configured to deliver a pharmaceutical or therapeutic substance to a target area. Such substance may be for instance an antibiotic, anti-coagulant or growth inhibitor. A balloon may be deployed to a target area in a vessel and inflated to contact an inner wall of the vessel to thereby deliver the pharmaceutical substance. However, although such balloon devices effectively can deliver drugs to a target area in a patient's vessel, the vessel is blocked by the balloon. Therefore, the time of contact of the drug eluting device with the vessel is limited to a short period of time, such as 30 to 60 seconds. This is particularly delicate in applications concerning a patient's heart, such as treatment of a coronary artery.

SUMMARY OF THE INVENTION

It is therefore an object of the present invention to provide a blood pump wherein a backflow of blood can be at least reduced or preferably prevented, it being preferable to provide a blood pump that is able to occlude a patient's vessel without causing harm to the vessel.

This object is achieved according to the present invention by a blood pump having the features of independent claim 1. Preferred embodiments and further developments of the invention are specified in the claims dependent thereon.

According to the invention, the blood plump comprises an outflow cannula having an upstream end portion, a downstream end portion and an intermediate portion extending between the upstream end portion and the downstream end portion. The upstream end portion of the outflow cannula is connected to the pump casing such that blood is conveyed from the blood flow outlet of the pump casing into and through the intermediate portion of the outflow cannula towards the downstream end portion of the outflow cannula, wherein the downstream end portion has a blood flow outlet through which blood can exit the outflow cannula.

At least a portion of the intermediate portion of the outflow cannula has an outer diameter that is larger than an outer diameter of the pump casing. Therefore, by providing an outflow cannula with an enlarged diameter it is possible to avoid or at least reduce a backflow of blood past the blood pump. The outflow cannula is able to act as an occlusion device, so that no additional occlusion device or blocking means are necessary.

The outflow cannula's intermediate portion may be sized and shaped to con-tact an inner wall of a patient's vessel in which the blood pump is placed during operation of the blood pump, in order to occlude the vessel during operation of the blood pump. It is advantageous to use the outflow cannula to occlude the vessel, in particular its intermediate portion, because forces that act on the inner wall of the vessel are distributed over a relatively large area in particular compared to e.g. a narrow ring-shaped occlusion device. Harm to the vessel can be avoided or at least reduced. In addition, the occlusion pressure is governed by the pump outflow dynamics and by the size of the outflow aperture. As such the occlusion pressure could be adjusted to just a few millimeters of mercury (mmHg) above the surrounding blood pressure. Preferably, the occlusion pressure will be in the range of 5-15 mmHg above the surrounding blood pressure.

The dimension of the blood pump may be selected appropriately for different applications of the blood pump. In one embodiment, the diameter of the outflow cannula's intermediate portion is at least twice as large as the diameter of the pump casing, preferably three times, more preferably four times. In another embodiment, the diameter of the outflow cannula's intermediate portion may be at least 1.1 times the pump casing diameter, preferably 1.5, more preferably twice as large as the diameter of the pump casing. A small diameter of the pump casing relative to the diameter of the outflow cannula's intermediate portion helps in preventing the pump casing from contacting the inner wall of a vessel. This in particular will also help to separate the inflow aperture of the pump away from the vessel wall. The risk of local vessel collapse and suck down into the pump can be eliminated. This can be particularly advantageous if the cannula is made e.g. from a softer material than the pump casing, which helps to prevent harm to the vessel. In reality, the system has a self-limiting suction. As suction starts to occur, the pump pressure is reduced which leads to cannula deflation and restoration of normal pressure throughout the vessel. The diameter of the outflow cannula's intermediate portion, in particular a largest diameter thereof, may be between about 5 mm and 2 cm, preferably between about 1 and 1.5 cm. For instance, if the blood pump is used in a renal vein that may have a diameter of about 1 cm, the outflow cannula's intermediate portion may have a diameter of about 1.1 or 1.3 cm to provide occlusion of the renal vein. In another embodiment, in particular if the blood pump is used in a heart vessel, such as a coronary artery, the diameter of the outflow cannula's intermediate portion, in particular a largest diameter thereof, may be between about 0.5 and 5 mm, preferably about 2 mm, which is appropriate for use in a coronary artery.

The blood flow outlet of the outflow cannula's downstream end portion is arranged at least partially radially inwards relative to an outermost circumference of the outflow cannula's intermediate portion. For instance, the downstream end portion may be tapered radially inwardly. This helps to provide a blood flow at least partially in an axial direction. This arrangement of the blood flow outlet prevents the blood flow outlet from being blocked when the outflow cannula is pressed against a vessel's inner wall. The blood flow outlet may be disposed in the downstream end portion, such that blood can exit the outflow cannula at least partially in an axial direction.

In an embodiment, a longitudinal length of the outflow cannula's intermediate portion may be less than 5 cm, preferably less than 2 cm. This length may be appropriate for use e.g. in a renal vein. Alternatively, a longitudinal length of the outflow cannula's intermediate portion is between about 1 and 3 mm. This length may be appropriate for use e.g. in a coronary artery. In particular, the longitudinal length of the outflow cannula's intermediate portion may be the length of the outflow cannula along which the intermediate portion contacts a respective vessel to preferably occlude the vessel.

In a preferred embodiment, a cross-sectional area of the blood flow outlet of the outflow cannula's downstream end portion is smaller than a cross-sectional area of the outflow cannula's intermediate portion, in particular a largest cross-sectional area of the outflow cannula's intermediate portion. Preferably, the cross-sectional area of the blood flow outlet of the outflow cannula's downstream end portion is less than 50%, preferably less than 40%, more preferably less than 30%, of the cross-sectional area of the outflow cannula's intermediate portion. The reduced diameter can be achieved for instance by providing at least two openings, preferably three openings, more preferably four openings, in the blood flow outlet of the outflow cannula. If more than one opening is provided, the cross-sectional area of all openings together forms the cross-sectional area of the outflow cannula's blood flow outlet. It will be appreciated that the outflow cannula's blood flow outlet may comprise more than four openings or a single opening which has a cross-sectional area smaller than that of the outflow cannula's intermediate portion.

A reduced cross-sectional area of the outflow cannula's blood flow outlet compared to the cross-sectional area of the outflow cannula's intermediate portion leads to a necking of the outflow and, thus, a filling of the outflow cannula and an increase of pressure within the outflow cannula. Thereby, the wall of the outflow cannula is biased radially outwardly towards the inner wall of the vessel in which it is placed. The outflow cannula unfolds or even expands to act as an occlusion device. This occurs automatically during operation of the pump. No additional inflation device is necessary to expand the pump in order to occlude the vessel.

Preferably, the outflow cannula is made of a softer material than the pump casing. The material of the outflow cannula may be a flexible, elastic, expandable, resilient or compliant material. Such material reduces harm to the patient's vessel in which the blood pump is placed. Furthermore, a soft material is advantageous to allow the outflow cannula to unfold or expand and to contact an inner wall of a patient's vessel. The material may also be non-compliant. The outflow cannula may also have a combination of different materials, e.g. to allow the outflow cannula to expand differently in different sections. For example the material may have anisotropic characteristics allowing for radial compliance but not axial compliance or vice versa. A soft and compliant cannula further helps to size the cannula to the right outer diameter. Just a small pressure difference between the inside of the cannula and the surrounding blood pressure will lead to an adjusted diameter of the cannula and will make it occlusive to the surrounding vessel wall even if it is physically undersize.

Pump vibration and the transmission of these vibrations are the main cause of harm to a blood vessel, especially when the contact area is minimal as in the case of a ring balloon. The present invention provides a greater isolation from the pump vibration due to the larger contact area and soft cannula wall that is incapable of transmitting vibration as is the case in a stiff balloon. The fact that the contact area between the vessel and the occlusive element in the device is increased in the present invention, a lower contacting force is needed.

In an embodiment, at least one of the outflow cannula's upstream end portion and the outflow cannula's downstream end portion may be tapered or conical, that is to say, a diameter of the outflow cannula may decrease towards one or both of the upstream and downstream ends. In other words, the diameter of the outflow cannula increases from the pump casing to the intermediate portion and decreases from the intermediate portion to the downstream end. This may improve and facilitate placement of the blood pump within a patient's vessel, e.g. by means of a catheter. The pump casing may be cylindrical or substantially cylindrical or may have any other appropriate shape. A tapered or conical shape of the downstream end portion may also be provided, such that the blood flow outlet, through which blood can exit the outflow cannula, opens at least partially in an axial direction, in order to prevent blocking of the blood flow outlet when the outflow cannula is pressed against an inner wall of a vessel.

The pump casing and the outflow cannula may be formed separately, with a minimum inner diameter of the upstream end portion preferably corresponding to an outer diameter of the pump casing such that the outflow cannula is sealingly connected to the pump casing. Any appropriate connection between the pump casing and the outflow cannula is possible that provides a fluid-tight connection, e.g. a press-fit, adhesive, welded connection, etc. The pump casing and the outflow cannula may be formed of the same or different materials. The pump casing and the outflow cannula may alternatively be formed integrally.

In a preferred embodiment of the blood pump, a support structure, such as a padding device may be provided that is arranged around at least a portion of the outflow cannula's intermediate portion. The padding device may be a circumferential pad. The pad may be formed of a soft material or may be hollow. In the latter case it may be filled with a fluid. The pad may be substantially cylindrical or conical. In other words, circumferential walls may be parallel or non-parallel, such that the pad is tapered. In case the pad is tapered, its diameter preferably increases in the direction of flow. Due to its soft properties, which are independent of the blood pressure within the outflow cannula, the pad may better conform to the shape of the inner wall of a vessel in which the blood pump is placed in order to improve occlusion of the vessel. The pad may comprise a special material that is impregnated or coated with a gel material that reduces the friction between the pad and the vessel wall.

In an embodiment, a drug eluting device may be included in the blood pump, the drug eluting device being configured to deliver a pharmaceutical substance to a target area in a patient. In an embodiment, the support structure may act as a drug eluting device or drug delivering device, i.e. the support structure, which may be formed as a padding device, may comprise a pharmaceutical substance, i.e. a medicament. The drug eluting device may be formed as at least one pad, in particular a single circumferential pad or two or more discrete pads, which comprises the pharmaceutical substance. The pad is configured to deliver the pharmaceutical substance to the surrounding tissue, in particular the inner wall of a patient's vessel which is contacted by the pad.

In an embodiment, the pad may have openings or may have a wall that is permeable for the medicament. The pad may comprise a continuous or porous material. The drug eluting device may comprise at least one reservoir that is fillable with a pharmaceutical substance. An access lumen, such as a tubular access may be provided to inject drugs into the reservoir or to remove drugs therefrom or both. The reservoir may be at least partially open on a radially outer surface to form a recess for receiving the drugs. Providing a drug eluting pad is particularly advantageous in delicate applications, such as in a heart vessel, like a coronary artery.

The blood pump may be connected to a catheter, in particular for insertion of the blood pump into a patient's vessel and for supplying electricity to a motor of the pump. The catheter may extend from the pump casing in the downstream direction, i.e. the direction of flow, through the outflow cannula and through an aperture in the downstream end portion of the outflow cannula, in particular along a longitudinal axis of the blood pump. Depending on the application, the catheter may alternatively extend in the opposite direction from the pump casing, i.e. the catheter may extend from the pump casing in the upstream direction, i.e. against the direction of flow. In this case, for guiding purposes, an extension may extend through the outflow cannula terminating in an atraumatic tip, such as a "J-tip" or "pigtail". In any case, the blood pump may be an axial blood pump, a centrifugal blood pump or a mixed-type blood pump.

The above described blood pump can advantageously be used as a renal pump, configured to be placed in a patient's renal vein to pump blood from a patient's kidney towards the patient's inferior vena cava. In this case, the outflow cannula may have an outer diameter in the range of about 1 to 2 cm, preferably about 0.75 to 1.5 cm. However, the blood pump is not restricted to this use but may also be used as any other organ pump, such as hepatic pump, or may be used e.g. in one of a patient's pulmonary arteries or coronary arteries. In case the blood pump is applied in a coronary artery, the outer diameter of the outflow cannula may be in the range of about 0.5 to 3 mm, preferably about 1.5 mm.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings:

FIG. 1b shows a perspective view of the blood pump of FIG. 1a.

FIG. 2a shows a cross-sectional view of the pump casing of the blood pump of FIG. 1a.

FIG. 2b shows a perspective view of the pump casing of the blood pump of FIG. 1a.

FIG. 3 shows a perspective view of the blood pump of FIG. 1a.

FIG. 6b shows an enlarged view of a detail of FIG. 6a.

FIG. 7b shows a perspective view of the blood pump of FIG. 7a.

FIG. 8b shows a perspective view of the blood pump of FIG. 8a.

FIG. 9 shows a perspective view of the pump casing of the blood pump of FIG. 8a.

FIG. 10 shows another perspective view of the pump casing of the blood pump of FIG. 8a.

FIG. 11 shows a perspective view of the impeller of the blood pump of FIG. 8a.

FIG. 13b shows an enlarged view of a detail of FIG. 13a.

DETAILED DESCRIPTION

Figure 1A:
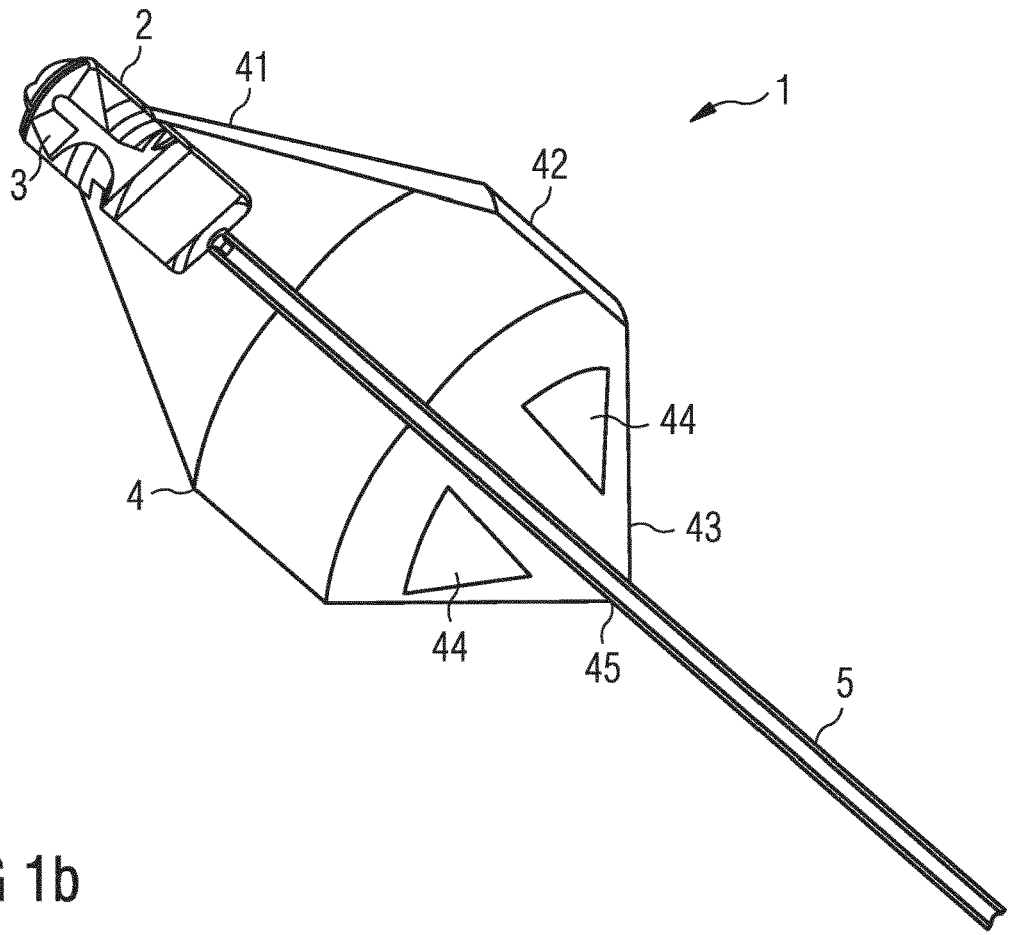
FIG. 1a shows a cross-sectional view of a blood pump according to the invention.
Figure 1B:
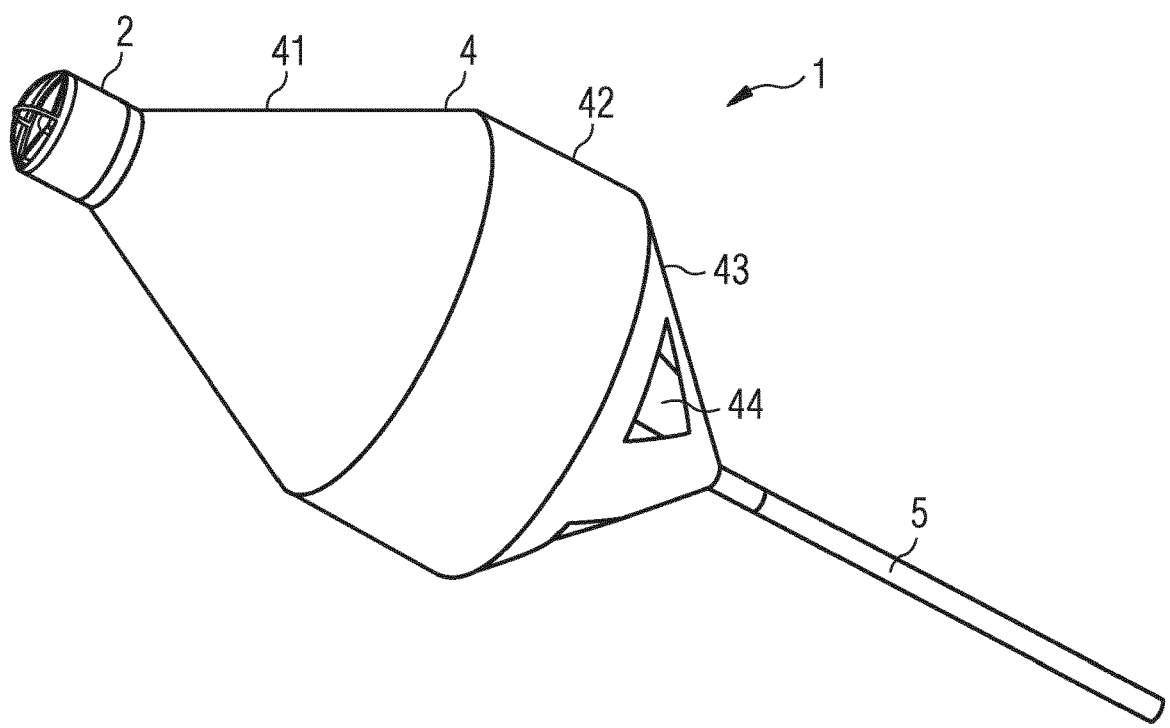

Referring to FIGS. 1a and 1b, a blood pump 1 according to the invention is shown. The blood pump 1 comprises a pump casing 2 with a rotatable impeller 3 and an outflow cannula 4 connected to the pump casing 2. The outflow cannula 4 has an upstream end portion 41, a downstream end portion 43 and an intermediate portion 42 extending therebetween. The upstream and downstream end portions 41 and 43 may be tapered to facilitate insertion of the blood pump 1 into a patient's vessel. The cannula 4 will be collapsed during insertion. Therefore, the taper may enhance the flow pattern of the pump 1. The taper at the upstream end portion 41 may allow the pump to wedge itself in a smaller vessel. The pump casing 2 may be cylindrical. However, it will be appreciated that other appropriate designs and shapes are possible as long as they achieve the function of the blood pump 1 according to the invention as described in more detail below. A catheter 5 is connected to the blood pump 1 to deploy it within a patient's vessel and to supply the blood pump 1 with electric energy. Upon rotation of the impeller 3, blood is drawn into the blood pump 1 through the pump casing 2, into the outflow cannula 4 and out of the blood pump 1 through openings 44 in the downstream end portion 43 of the outflow cannula 4 as indicated by arrows in FIG. 6b.

Figure 2A:
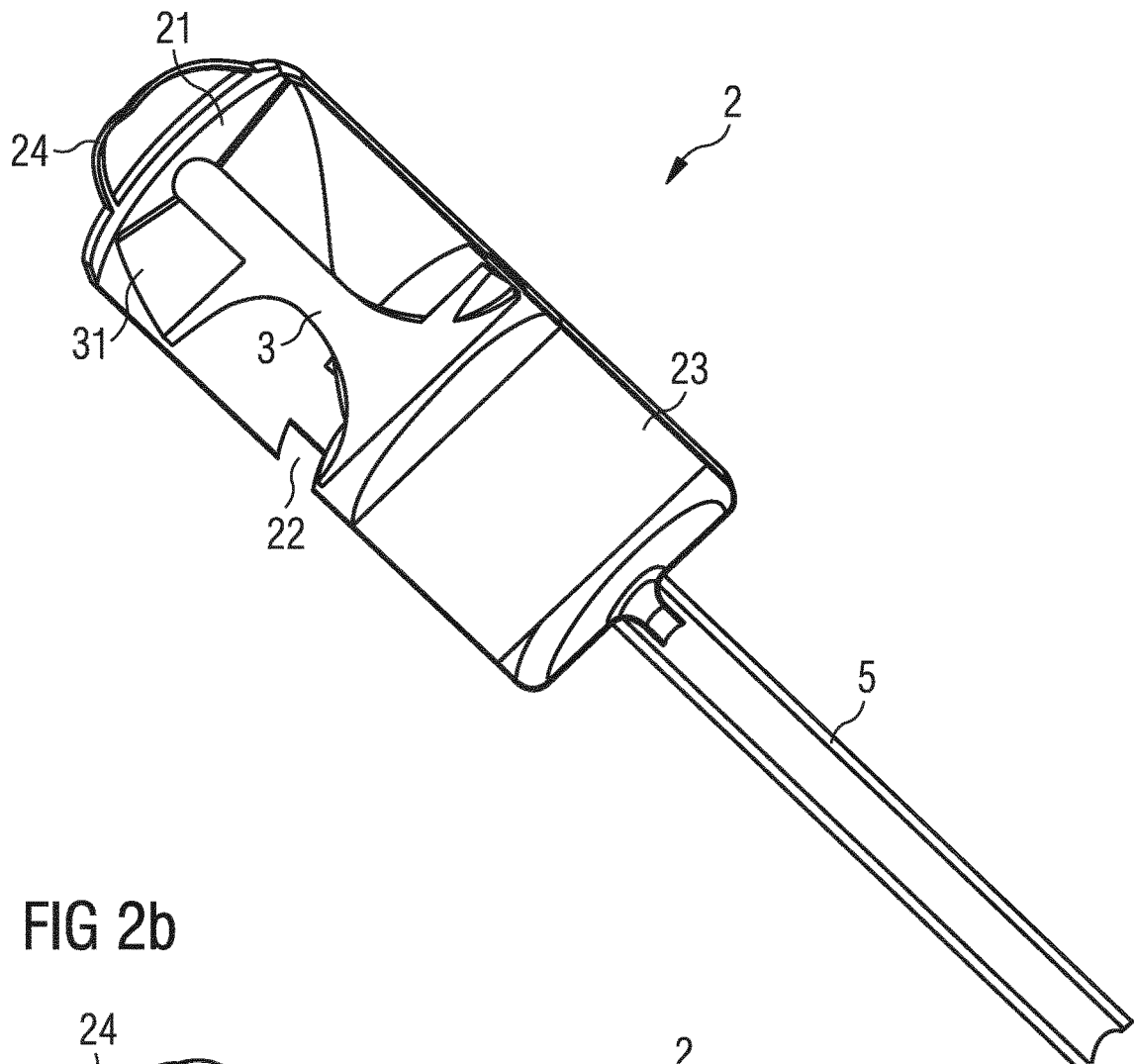
Figure 2B:
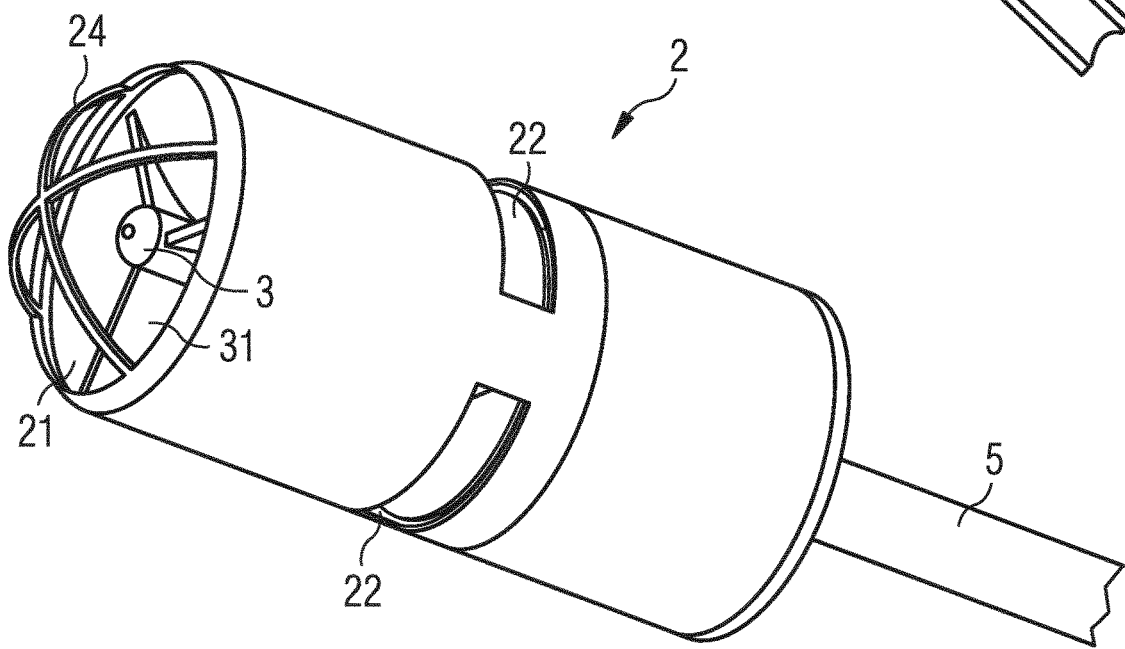

FIGS. 2a and 2b show the pump casing 2 of the blood pump 1. The pump casing 2 has a blood flow inlet 21 and a blood flow outlet 22. In this embodiment, the blood flow inlet 21 is an axial opening spanned by a protection structure 24, such as a grill to prevent soft tissue from entering the blood flow inlet 21. It will be appreciated that any other suitable means for preventing soft tissue from entering the pump casing 2 can be chosen. The blood flow outlet 22 is formed by radial openings spaced from the blood flow inlet 21 along the longitudinal direction in the direction of flow. Thus, the blood pump 1 can be considered a mixed-type blood pump, where the blood flow has axial and radial components. However, the blood pump may also be formed as an axial or centrifugal blood pump. As can be seen in FIG. 1a, the outflow cannula 4 is connected to the pump casing 2 such that the blood flow outlet 22 is disposed inside the outflow cannula 4 to cause a blood flow into and through the outflow cannula 4. The impeller 3 is disposed within the pump casing 2 and has blades 31 to convey blood from the blood flow inlet 21 to the blood flow outlet 22. Rotation of the impeller 3 is caused by a drive unit 23, such as an electric motor. The drive unit may alternatively be provided outside the blood pump, in which case rotation is transmitted via a flexible drive cable located inside (not shown) catheter 5 from an external drive unit to the impeller. FIG. 3 is a perspective view of the blood pump 1, showing in particular the downstream end portion 43 of the outflow cannula 4 having openings 44 for the blood flow and an aperture 45 for receiving the catheter 5. The openings 44 together form a smaller cross-sectional area than the intermediate portion 42. Thus, during operation of the blood pump 1, pressure is increased in the outflow cannula 4 such that the outflow cannula 4 is unfolded or even expanded or inflated. Due to the comparatively large diameter of the outflow cannula 4, the outflow cannula 4 is caused to contact an inner wall of a patient's vessel, thereby sealing and occluding the vessel to prevent blood from flowing in a backward direction. In this embodiment, four openings 44 are shown. It will be appreciated that there may be only a single opening, two or three, or more than four openings as long as sufficient pressure stasis is caused to unfold or expand the outflow cannula 4 and press it against the inner wall of a vessel in which the blood pump 1 is placed. A pressure difference between the inside and outside of the outflow cannula 4 may be for instance about 20 mmHg. Preferably, however, this differential pressure will not exceed 15 mmHg.

Figure 4A:
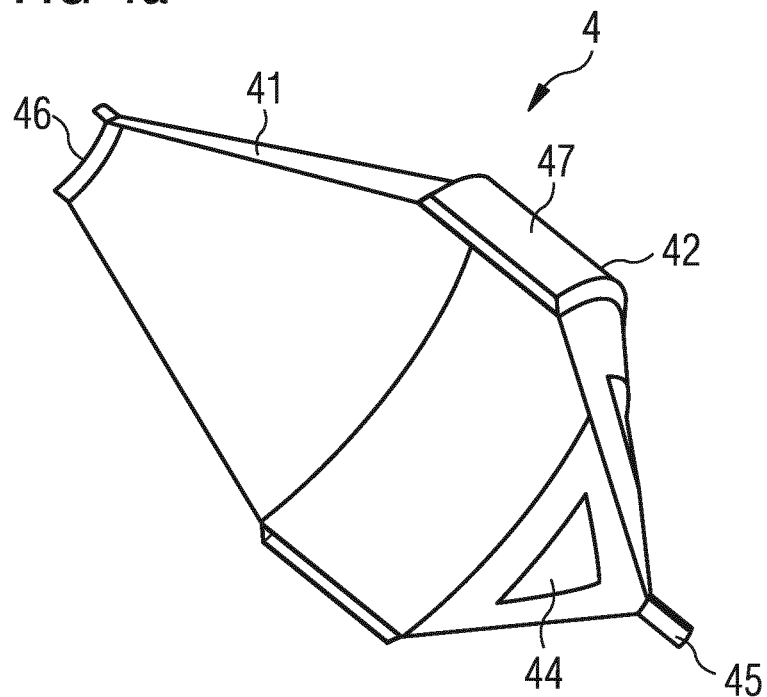
FIG. 4a shows a cross-sectional view of an embodiment of the outflow cannula.
Figure 4B:
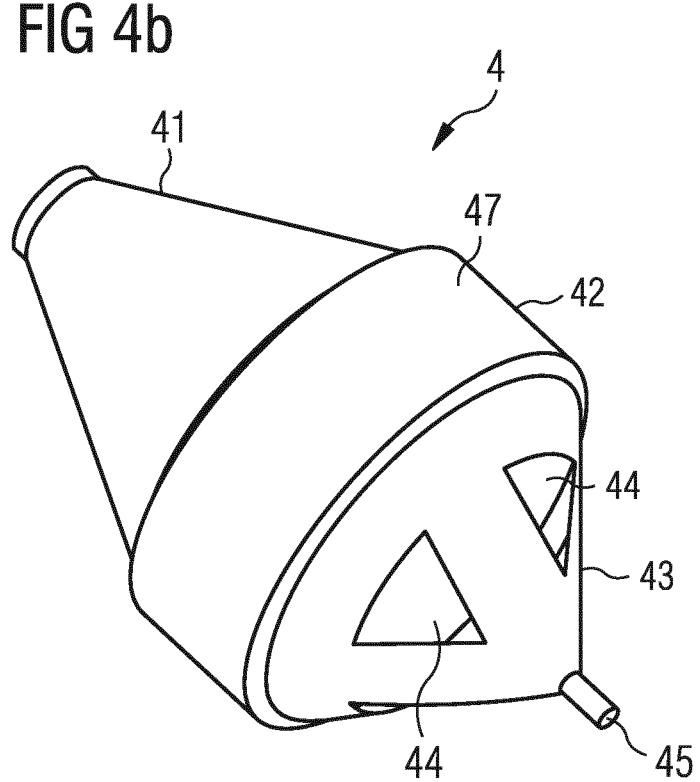
FIG. 4b shows a perspective view of an embodiment of the outflow cannula.
Figure 5A:
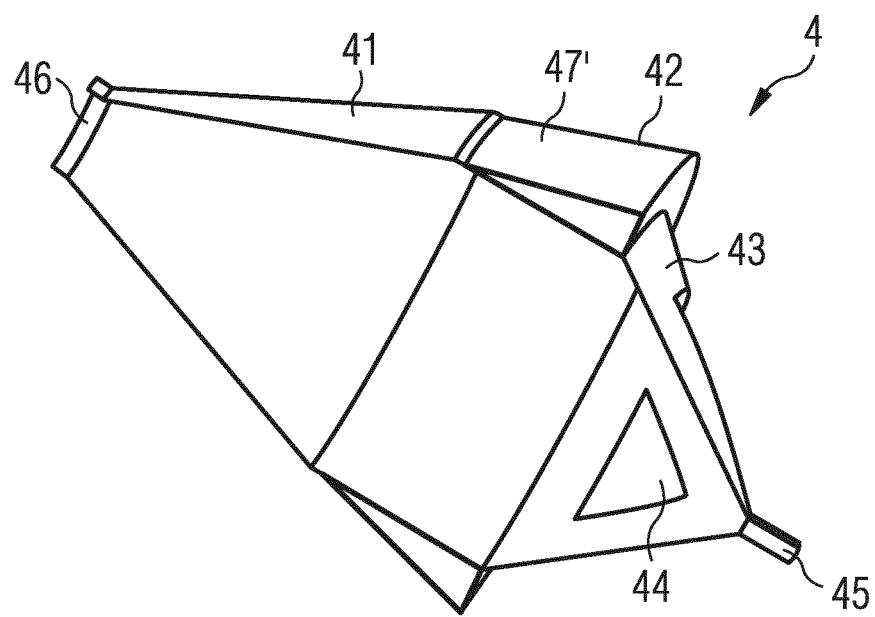
FIG. 5a shows a cross-sectional view of another embodiment of the outflow cannula.
Figure 5B:
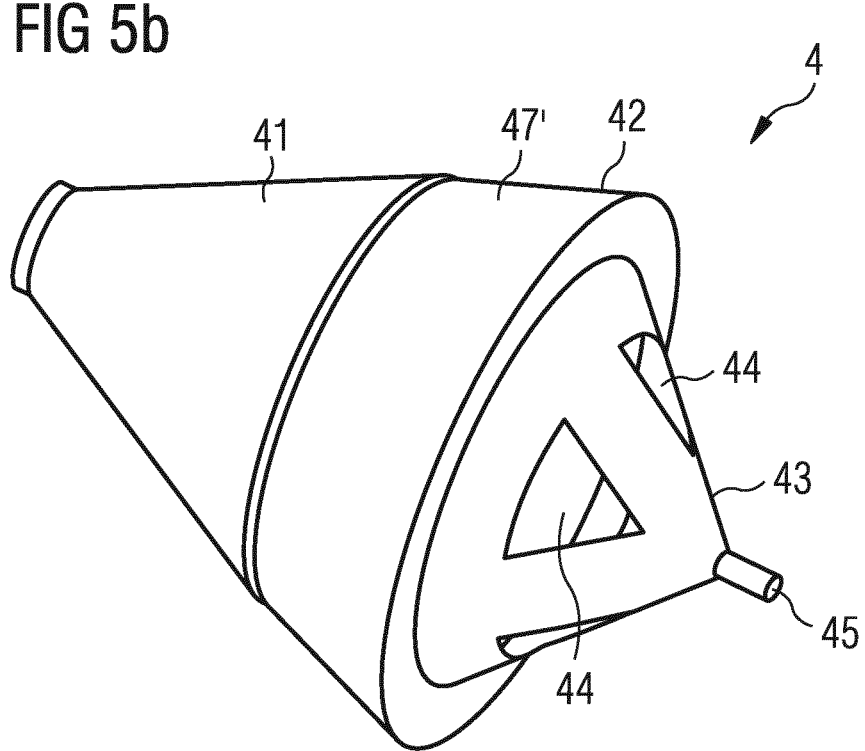
FIG. 5b shows a perspective view of another embodiment of the outflow cannula.

In order to improve the valve function of the outflow cannula 4, that is to say, in order to improve the sealing contact between the outflow cannula 4 and the patient's vessel, a pad 47 may be provided as shown in FIGS. 4a, 4b. The pad 47 is arranged around the circumference of the intermediate portion 42 of the outflow cannula 4. It may be made of a soft material or may be hollow and filled with a fluid. The pad 47 allows the outflow cannula 4 to better conform to the shape of the patient's vessel independently of the blood pressure within the outflow cannula 4. FIGS. 4a and 4b show an embodiment in which the pad 47 is substantially cylindrical. It may extend over the entire intermediate portion 42 or only over a part of it, in particular with respect to the longitudinal direction. A similar embodiment is shown in FIGS. 5a and 5b, it being identical to the previous embodiment except for the shape of the pad. The pad 47' is tapered or wedge-shaped with a diameter of the pad 47' increasing in the direction of flow. This shape may improve occlusion of the vessel in which the blood pump 1 is placed.

Figure 6A:
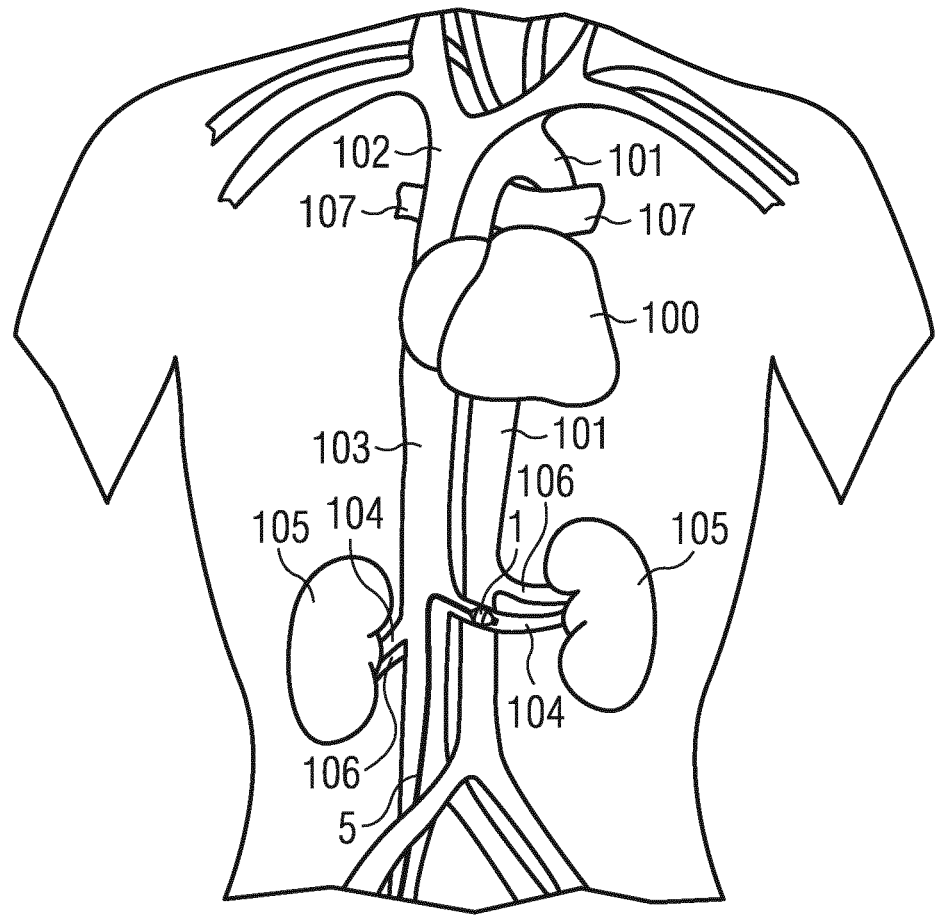
FIG. 6a shows the blood pump of FIG. 1a placed in a patient's renal vein.
Figure 6B:
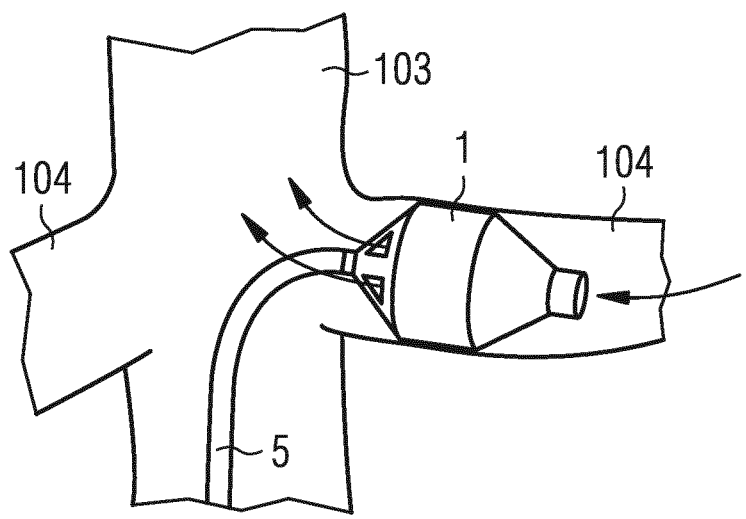

An application of the blood pump 1 is shown in FIGS. 6a and 6b. The blood pump 1 is used as a renal pump to pump blood from a patient's kidney 105 through the renal vein 104 towards the inferior vena cava 103. FIG. 6a also shows the patient's heart 100, the aorta 101 and the superior vena cava 102. As can be seen particularly in FIG. 6b, the blood pump 1 fully occludes or blocks the renal vein 104. A typical diameter of the renal vein is about 1 cm. Thus, an appropriate diameter of the intermediate portion 42 of the outflow cannula 4 would be about 1.1 or 1.5 cm. The blood pump 1 according to the invention can prevent a backflow of blood towards the kidney 105 and, therefore, effectively pump blood towards the inferior vena cava 103. This treatment can be applied in case a patient suffers from malfunction of the left or right ventricle, which may lead to high blood pressure in the vena cava and, therefore, to kidney failure because of poor blood flow away from the kidney. The blood pump 1 supports this blood flow. The blood flow caused by the blood pump 1 may be for instance between about 0.5 and 2 liters per minute. It will be appreciated that other applications of the blood pump are possible, e.g. in a pulmonary artery.

In other applications, for example if the blood pump is to be placed in the renal artery 106 or in the pulmonary artery 107, a reverse flow configuration may be needed. That is to say, the blood pump in a reverse flow configuration pumps the blood in an opposite direction compared to the previously discussed embodiments. While in the previously discussed embodiments the blood is pumped towards the catheter, it may be necessary in other applications to pump the blood in a direction away from the catheter due to restricted access possibilities in the human body. Also if a blood pump is to be placed in a patient's coronary artery, a reverse flow configuration is needed.

Figure 7A:
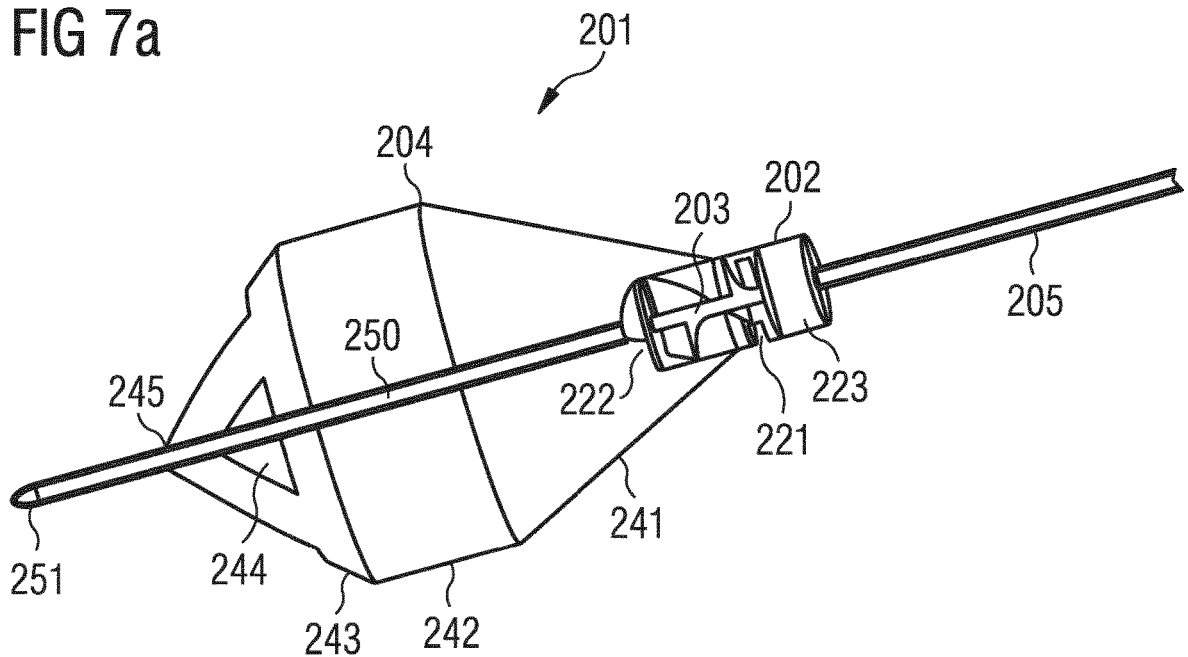
FIG. 7a shows a cross-sectional view of a blood pump according to another embodiment.
Figure 7B:
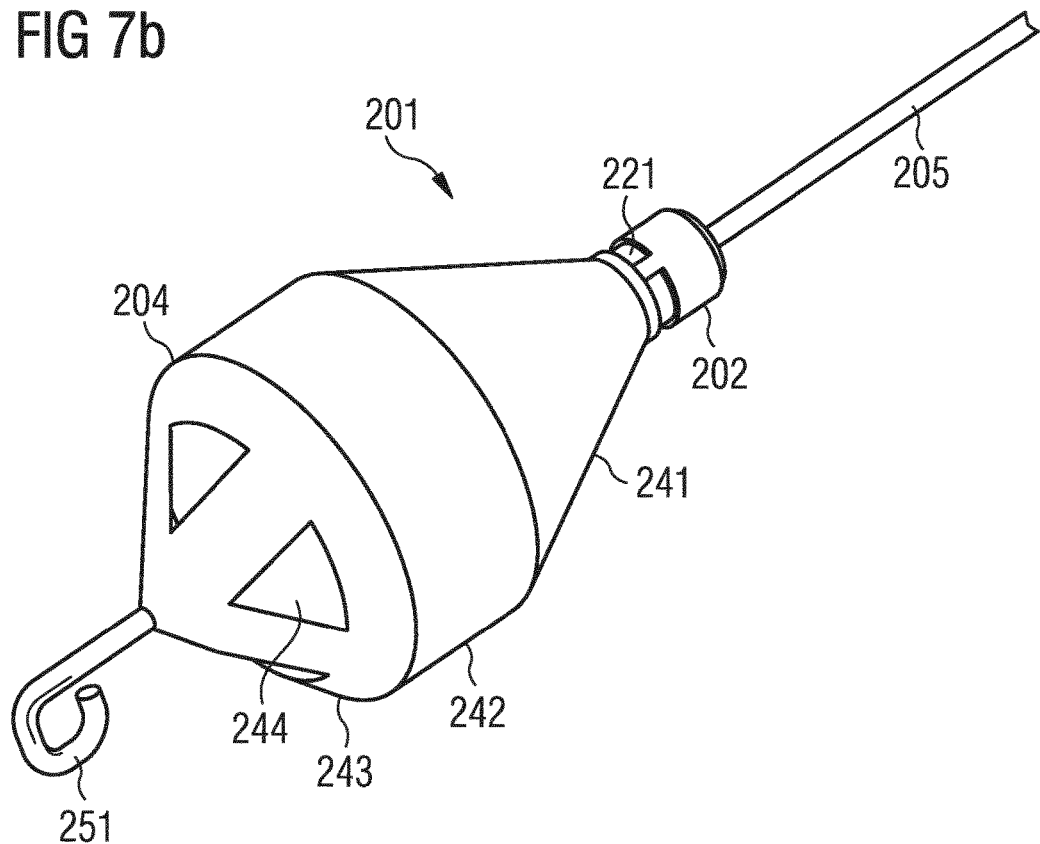
Figure 8A:
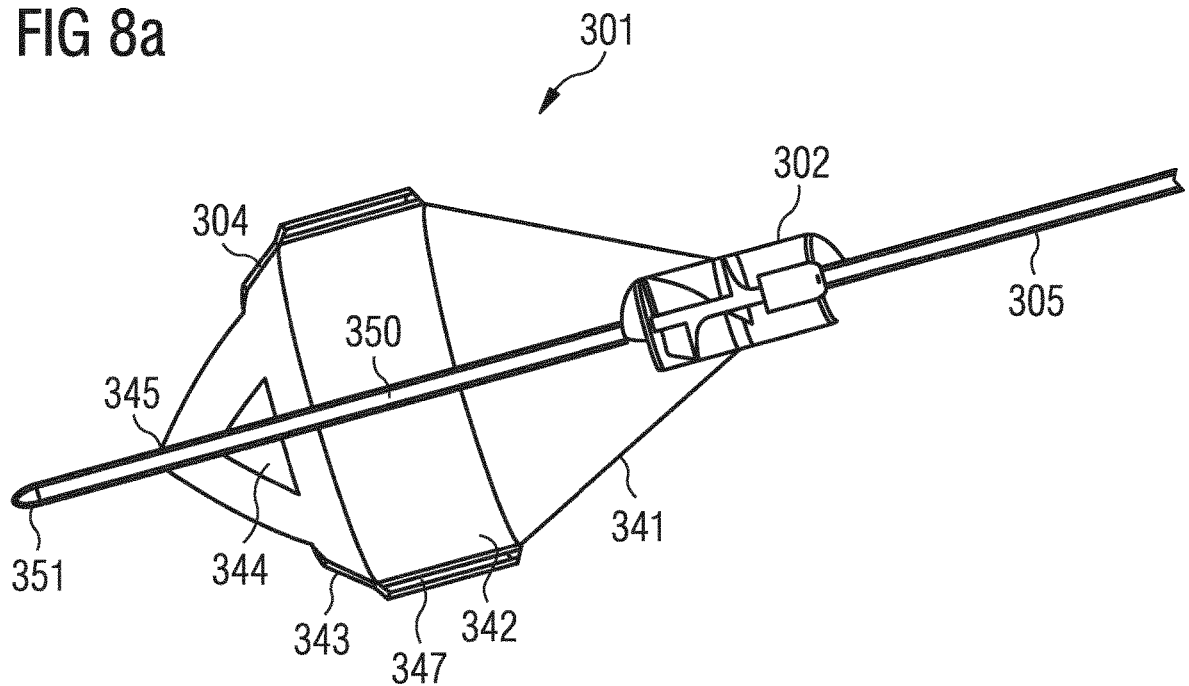
FIG. 8a shows a cross-sectional view of a blood pump according to another embodiment.
Figure 8B:
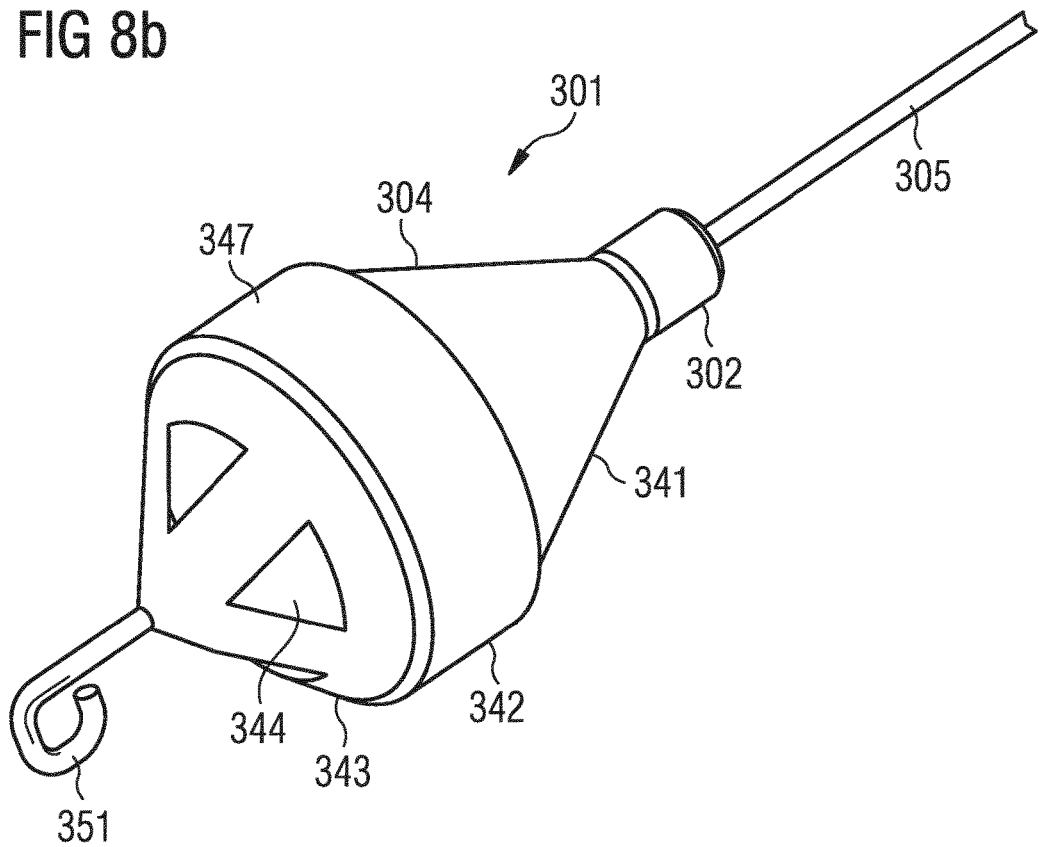

An embodiment that is similar to that of FIG. 1a but has an opposite direction of flow compared to the blood pump of FIG. 1a is shown in FIGS. 7a and 7b. The blood pump 201 comprises a pump casing 202 and an outflow cannula 204 having a larger diameter than the pump casing 202. An impeller 203 is arranged in the pump casing 202 and driven by a drive unit 223, such as an electric motor that is magnetically coupled to the impeller 203. The pump casing 202 is connected to a catheter 205. The impeller 203 conveys blood from a blood flow inlet 221 to a blood flow outlet 222 and into the outflow cannula 204. The blood flow inlet 221 is in close proximity to the outflow cannula 204 such that the larger diameter of the outflow cannula 204 helps keeping tissue of the vessel away from the blood flow inlet 221.

As in the previous embodiments, the outflow cannula 204 comprises an upstream end portion 241, an intermediate portion 242 and a downstream end portion 243. The downstream end portion 243 has openings 244 through which blood can exit the outflow cannula 204 as described in connection with the previous embodiments. Since the catheter 205 does not extend through the outflow cannula 204, a catheter extension 250 is provided that extends through the outflow cannula 204 and out of an aperture 245 in the downstream end portion 243 to be able to guide the blood pump 201 during insertion into the patient's vessel. An atraumatic tip 251, such as a J-tip or pigtail is disposed at the end of the catheter extension 250. The tip 251 prevents harm to the patient's vessel during insertion of the blood pump 201.

FIGS. 8a to 13b illustrate another embodiment of a blood pump 301. The structure of the blood pump 301 is similar to those described above, in particular the embodiment of FIGS. 7a and 7b with regards to the direction of flow. However, the blood pump 301 is in-tended to be used in a patient's coronary artery 108 (see FIGS. 13a, 13b). Thus, its diameter is smaller compared to e.g. a renal pump, for example about 2 mm. The blood pump 301 comprises a pump casing 302 connected to a catheter 305. A rotatable impeller 303 is disposed in the pump casing 302, and an outflow cannula 304 is connected to the pump casing 302. Due to the small diameter of the blood pump 301 the drive unit (not shown) is disposed external to the blood pump 301. Rotation of the drive unit is transmitted to the impeller 303 through the catheter 305 via a flexible drive shaft (not shown). Alternatively, for pumps with diameter between 3 and 5 mm a direct drive motor could be used, wherein the motor is situated right behind the pump. In this case a flexible drive shaft will not be required. Upon rotation of the impeller 303, blood is drawn into the blood pump 301 through the pump casing 302, into the outflow cannula 304 and out of the blood pump 301 through openings 344 in the downstream end portion 343 of the outflow cannula 304 as indicated by arrows in FIG. 13b.

The outflow cannula 304 has an upstream end portion 341, a downstream end portion 343 and an intermediate portion 342 extending therebetween. The upstream and downstream end portions 341 and 343 may be tapered to facilitate insertion of the blood pump 301 into the patient's vessel, such as a coronary artery. The cannula 304 will be collapsed during insertion. The taper at the downstream end portion 343 may allow the pump to wedge itself in a small vessel. The pump casing 302 may be cylindrical. However, it will be appreciated that other appropriate designs and shapes are possible as long as they achieve the function of the blood pump 301.

The catheter 305 does not extend through the outflow cannula 304 but is connected to the blood pump 301 at its inlet end. Thus, a catheter extension 350 is connected to the pump casing 302 that extends through the outflow cannula 304 and exits the outflow cannula 304 through an aperture 345 at the downstream end portion 343 so as to be able to guide the blood pump 301 through a patient's vessel by means of the catheter 305 during insertion of the blood pump 301. The catheter extension 350 is provided with an atraumatic tip 351, such as a J-tip or pigtail in order to prevent harm to the patient's vessel, such as puncturing of the vessel.

Figure 9:
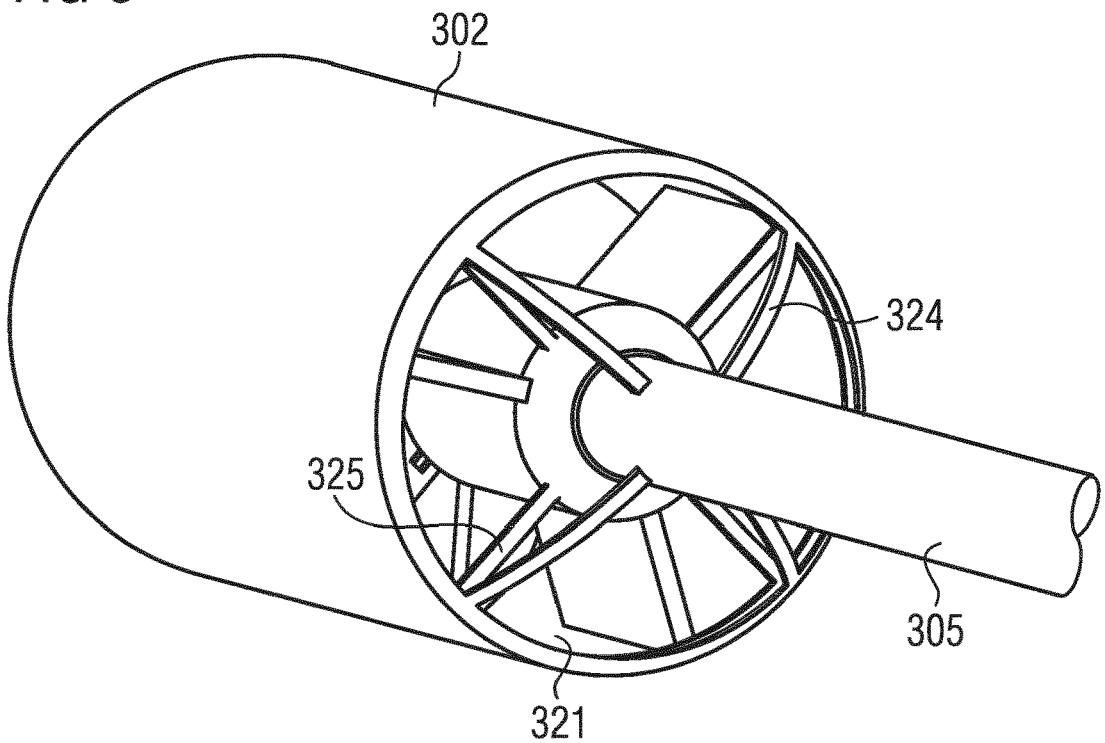
Figure 10:
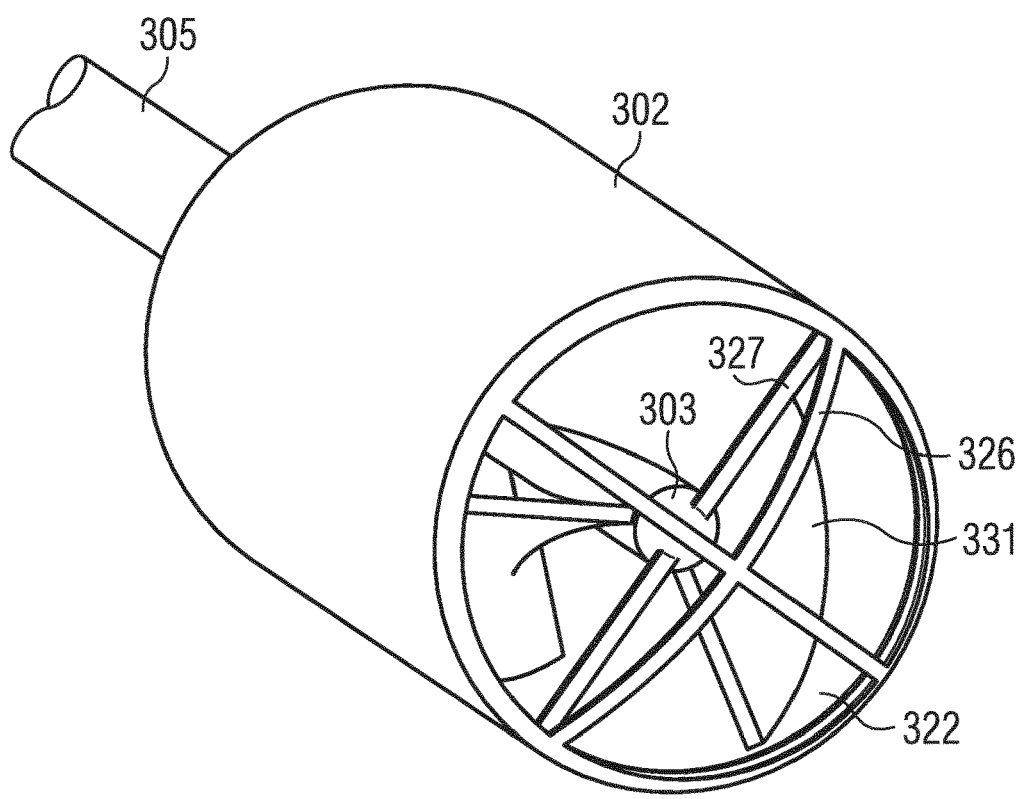

The pump casing 302 is illustrated in more detail in FIGS. 9 and 10. FIG. 9 is a perspective view of the blood flow inlet 321 of the pump casing 302, whereas FIG. 10 is a perspective view of the blood flow outlet 322 of the pump casing 302. In order to prevent suction of tissue into the pump casing 302, a protection structure, such as a grill 324 is disposed over the blood flow inlet 321. The grill 324 may have a curved shape. However, any other means to protect tissue from being sucked into the blood pump 301 can be provided. Likewise, a protection structure, such as a grill 326 is provided at the blood flow outlet 322 to protect the outflow cannula 304 or tissue from the rotating impeller 303. Struts 325 and 327 are provided at the inlet 321 and outlet 322, respectively, to support the grill 324 and 326 respectively.

Figure 11:
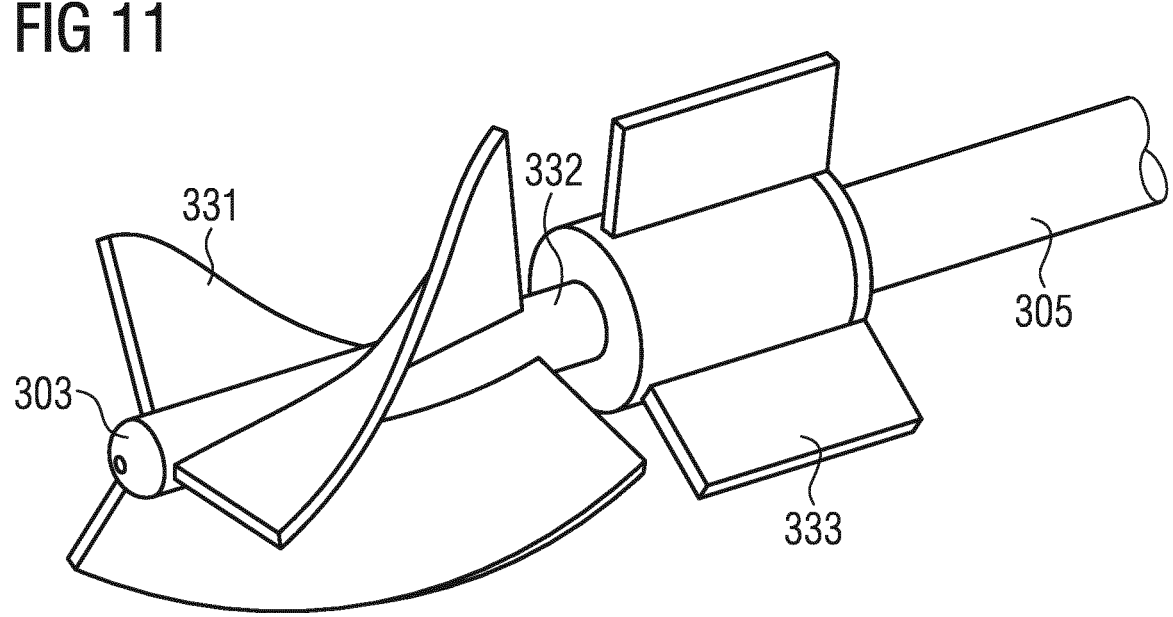

The impeller 303 is shown in more detail in FIG. 11. The impeller 303 is coupled to a drive shaft extending through the catheter 305 as explained in the aforementioned. Blades 331 are disposed on an impeller shaft 332 which convey blood from the pump casing's blood flow inlet 321 to the blood flow outlet 322 upon rotation of the impeller shaft 332. Stator blades 333 are provided at the upstream end of the impeller 303 in order to reduce turbulences of the blood flow and to engage and center the impeller 303 and the catheter 305 in the center of the pump casing 302. The stator blades 333 are either press fitted, welded, or bonded to the inside diameter of the pump casing 302. The center portion of the stator blades 333 serves as a bearing that engages the impeller shaft 332.

The blood pump 301 does not only function as a pumping device but also as a drug eluting device. Application of medicaments, such as anti-inflammatory, antibiotics, anticoagulants, or growth inhibitors is of particular importance in coronary artery applications. For this purpose, a drug eluting device, such as a drug eluting pad 347 is disposed on the outflow cannula 304. The outflow cannula 304 has a sufficiently large diameter to bring the drug eluting pad 347 close to the inner wall of the vessel. Preferably, the drug eluting pad 347 contacts the vessel wall or is pressed against it. In particular, this may be achieved by expanding the outflow cannula 304 as described in connection with the previous embodiments, wherein the outflow cannula 304 has a larger outer diameter than the pump casing 302. However, in some embodiments the outflow cannula 304 might not have a larger outer diameter than the pump casing 302.

Figure 12:
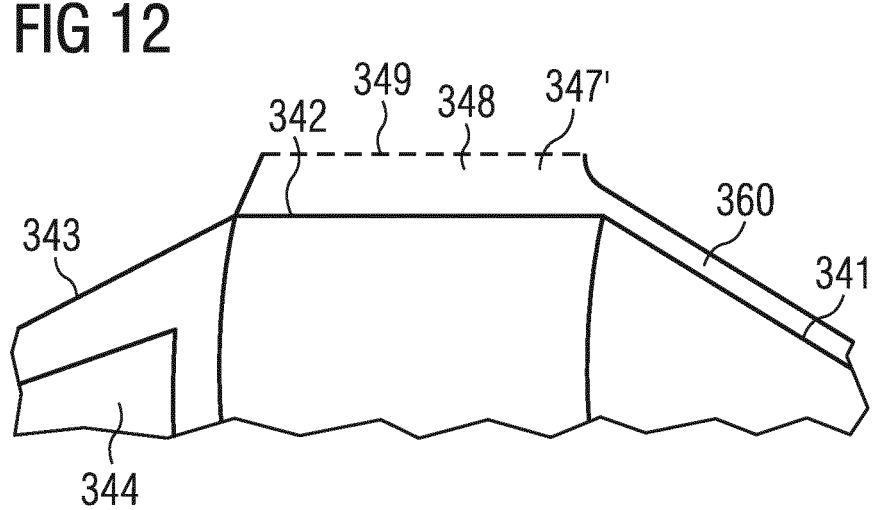
FIG. 12 shows a schematic partial view of an embodiment of the outflow cannula.

The drug eluting pad 347 may assume any suitable size and shape to deliver drugs to the target area. The drug eluting pad 347 may be tubular or ring shaped, or may comprise separate discrete portions. The pad 347 may be made of a continuous or porous material or may be hollow and filled with a substance comprising the drugs. The wall of the pad 347 may then comprise apertures or may be permeable to enable a desired amount of drugs to penetrate the wall of the drug eluting device. Since the drug eluting pad 347 is disposed on the outflow cannula 304 it can be brought into direct contact with the target area, such as the inner vessel wall. In another embodiment as shown in FIG. 12, the drug eluting device 347' may comprise a reservoir 348 that is connected to an access lumen, such as a tubular access 360 in order to inject drugs into the reservoir 348 or remove drugs therefrom. The reservoir 348 may be formed as a recess that is at least partially open at a surface facing the wall of the vessel. The reservoir 348 may have a plurality of apertures 349 to release the medicaments.

Figure 13A:
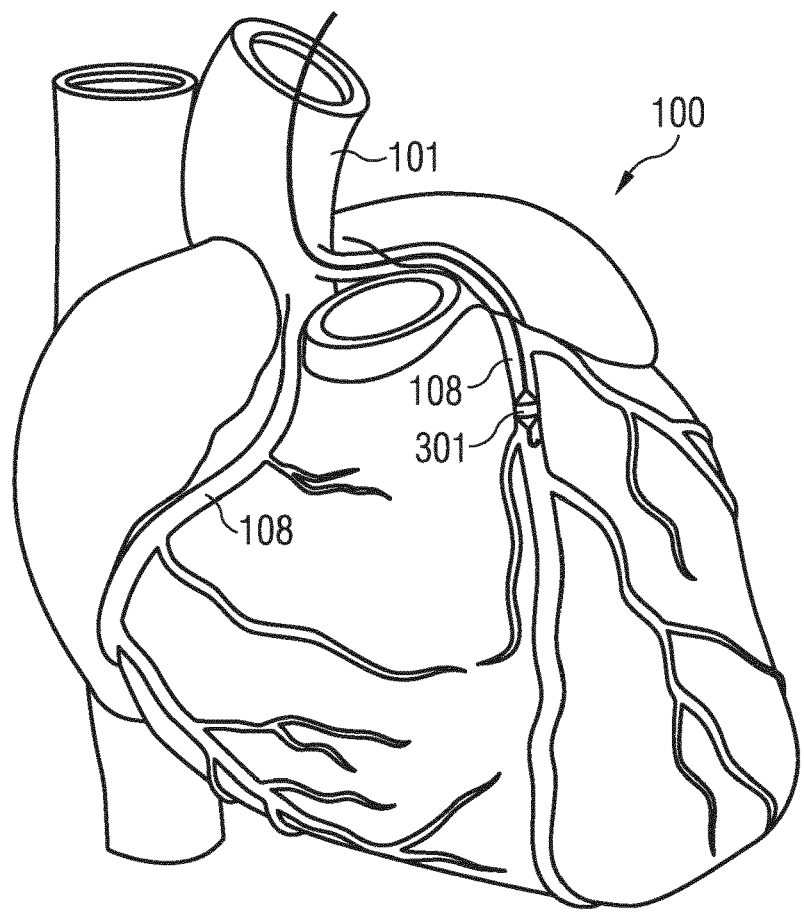
FIG. 13a shows the blood pump of FIG. 8a placed in a patient's coronary artery.
Figure 13B:
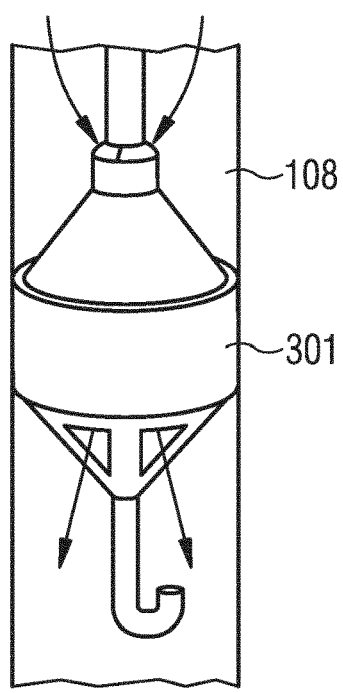

The blood pump 301 is particularly designed for an application in a patient's coronary artery 108 as shown in FIGS. 13a and 13b. It is inserted through the aorta 101 towards at the patient's heart 100 and into one of the coronary arteries 108, which may have been blocked due to a stenosis. Drugs can be effectively delivered to the coronary artery 108 by means of the drug eluting pad 347. The coronary artery 108 is not blocked as by known balloon devices because the blood pump 301 ensures a blood flow through the coronary artery 108. Therefore, the blood pump 301 can be kept in the coronary artery 108 for a sufficiently long time to deliver a desired amount of medicaments.

The invention claimed is:

1. A blood pump configured to be placed in a renal vein of a patient to pump blood from a kidney of the patient towards an inferior vena cava of the patient, the blood pump comprising:
   a pump casing having a blood flow inlet and a first blood flow outlet;
   an impeller arranged in the blood pump casing so as to be rotatable about an axis of rotation for conveying blood from the blood flow inlet to the first blood flow outlet;
   an outflow cannula having an upstream end portion, a downstream end portion and an intermediate portion extending between the upstream end portion and the downstream end portion; and
   a support structure that is arranged around at least a portion of the intermediate portion of the outflow cannula, wherein the support structure is at least one of a substantially cylindrical and a substantially conical pad, and wherein the support structure is configured to improve occlusion of the renal vein by the blood pump,
   wherein the upstream end portion of the outflow cannula is connected to the pump casing such that blood is conveyed from the first blood flow outlet into and through the intermediate portion of the outflow cannula towards the downstream end portion of the outflow cannula, wherein the downstream end portion of the outflow cannula has a second blood flow outlet through which blood can exit the outflow cannula and which is arranged at least partially radially inwards relative to an outermost circumference of the intermediate portion of the outflow cannula, wherein at least a portion of the intermediate portion of the outflow cannula has an outer diameter that is larger than an outer diameter of the pump casing, and
   wherein at least the intermediate portion of the outflow cannula is sized and shaped to contact an inner wall of the renal vein of the patient in which the blood pump is placed during operation of the blood pump in order to occlude the renal vein during operation of the blood pump.

2. The blood pump of claim 1, wherein the second blood flow outlet is disposed in the downstream end portion, such that blood can exit the outflow cannula at least partially in an axial direction.

3. The blood pump of claim 1, wherein a cross-sectional area of the second blood flow outlet is smaller than a largest cross-sectional area of the intermediate portion of the outflow cannula.

4. The blood pump of claim 3, wherein the cross-sectional area of the second blood flow outlet is less than 50% of the cross-sectional area of the intermediate portion of the outflow cannula.

5. The blood pump of claim 1, wherein the outer diameter of the intermediate portion of the outflow cannula is at least 1.5 times as large as the outer diameter of the pump casing.

6. The blood pump of claim 1, wherein a largest diameter of the intermediate portion of the outflow cannula is between about 5 mm and 2 cm.

7. The blood pump of claim 6, wherein the largest diameter of the intermediate portion of the outflow cannula is between about 1 and 1.5 cm.

8. The blood pump of claim 1, wherein a longitudinal length of the intermediate portion of the outflow cannula is less than 5 cm.

9. The blood pump of claim 8, wherein the longitudinal length of the intermediate portion of the outflow cannula is less than 3 cm.

10. The blood pump of claim 1, wherein the outflow cannula comprises a material that is softer than a material of the pump casing.

11. The blood pump of claim 10, wherein the material of the outflow cannula is elastic.

12. The blood pump of claim 1, wherein at least one of the upstream end portion of the outflow cannula and the downstream end portion of the outflow cannula is tapered.

13. The blood pump of claim 1, wherein a minimum inner diameter of the upstream end portion of the outflow cannula corresponds to the outer diameter of the pump casing and the outflow cannula is sealingly connected to the pump casing.

14. The blood pump of claim 1, wherein the support structure comprises a pharmaceutical substance.

15. The blood pump of claim 1, wherein the support structure is configured to conform to a shape of the renal vein.

16. The blood pump of claim 1, comprising a drug eluting device, the drug eluting device being configured to deliver a pharmaceutical substance to a target area in a patient.

17. The blood pump of claim 16, wherein the drug eluting device comprises a reservoir that is connected to an access lumen for at least one of injecting and removing a pharmaceutical substance to or from the reservoir.

18. The blood pump of claim 16, wherein the drug eluting device at least partially surrounds the intermediate portion of the outflow cannula.

19. The blood pump of claim 16, wherein the drug eluting device is at least one of a substantially cylindrical and a substantially conical pad.

20. The blood pump of claim 1, wherein the blood pump is connected to a catheter that extends from the pump casing through the outflow cannula, or wherein the blood pump is connected to a catheter that extends from the pump casing in a direction away from the outflow cannula.

21. The blood pump of claim 1, wherein the blood pump is one of an axial blood pump, a centrifugal blood pump and a mixed-type blood pump.

22. The blood pump of claim 1, wherein the second blood flow outlet comprises at least two openings.

23. A method for supporting a blood flow in a renal vein of a patient using a blood pump configured to be placed in the renal vein of the patient to pump blood from a kidney of the patient towards an inferior vena cava of the patient, the blood pump comprising:
   a pump casing having a blood flow inlet and a first blood flow outlet;
   an impeller arranged in the blood pump casing so as to be rotatable about an axis of rotation for conveying blood from the blood flow inlet to the first blood flow outlet;
   an outflow cannula having an upstream end portion, a downstream end portion and an intermediate portion extending between the upstream end portion and the downstream end portion; and a support structure that is arranged around at least a portion of the intermediate portion of the outflow cannula, wherein the support structure is at least one of a substantially cylindrical and a substantially conical pad, and wherein the support structure is configured to improve occlusion of the renal vein by the blood pump, wherein the upstream end portion of the outflow cannula is connected to the pump casing such that blood is conveyed from the first blood flow outlet of the pump casing into and through the intermediate portion of the outflow cannula towards the downstream end portion of the outflow cannula, wherein the downstream end portion has a second blood flow outlet through which blood can exit the outflow cannula and which is arranged at least partially radially inwards relative to an outermost circumference of the intermediate portion of the outflow cannula, and wherein at least a portion of the intermediate portion of the outflow cannula has an outer diameter that is larger than an outer diameter of the pump casing, the method comprising the steps of:

operating the blood pump, when placed in the renal vein of the patient, such that at least the intermediate portion of the outflow cannula contacts an inner wall of the renal vein of the patient in which the blood pump is placed during operation of the blood pump so as to occlude the renal vein during operation of the blood pump.

\* \* \* \* \*